(12) United States Patent
Wang et al.

(10) Patent No.: US 10,033,821 B2
(45) Date of Patent: Jul. 24, 2018

(54) METHOD, APPARATUS, AND SYSTEM FOR PUSHING NETWORK CONTENT

(71) Applicant: ANHUI HUAMI INFORMATION TECHNOLOGY CO., LTD., Hefei, Anhui (CN)

(72) Inventors: Hui Wang, Hefei (CN); Wang Huang, Hefei (CN)

(73) Assignee: Anhui Huami Information Technology Co., LTD., Hefei (CN)

(*) Notice: Subject to any disclaimer, the term of this patent is extended or adjusted under 35 U.S.C. 154(b) by 466 days.

(21) Appl. No.: 14/737,714

(22) Filed: Jun. 12, 2015

(65) Prior Publication Data

US 2016/0105520 A1 Apr. 14, 2016

(30) Foreign Application Priority Data

Oct. 10, 2014 (CN) .......................... 2014 1 0531591

(51) Int. Cl.
| | | |
|---|---|---|
| *G06F 15/16* | (2006.01) | |
| *H04L 29/08* | (2006.01) | |
| *G06F 17/30* | (2006.01) | |
| *A61B 5/024* | (2006.01) | |
| *A61B 5/16* | (2006.01) | |
| *A61B 5/11* | (2006.01) | |

(52) U.S. Cl.
CPC .......... *H04L 67/26* (2013.01); *A61B 5/02438* (2013.01); *A61B 5/1118* (2013.01); *A61B 5/165* (2013.01); *G06F 17/30867* (2013.01); *H04L 67/22* (2013.01); *A61B 5/1116* (2013.01)

(58) Field of Classification Search
CPC ..... H04L 67/22; H04L 67/26; A61B 5/02438; G06F 17/30867
See application file for complete search history.

(56) References Cited

U.S. PATENT DOCUMENTS

| | | | |
|---|---|---|---|
| 7,412,202 B2 | 8/2008 | Gutta et al. | |
| 2012/0329432 A1* | 12/2012 | Gupta | G06Q 30/02 455/414.1 |
| 2015/0341453 A1* | 11/2015 | Miller | H04L 67/22 709/204 |
| 2016/0063101 A1* | 3/2016 | Kanda | G06F 17/30749 707/722 |
| 2016/0066858 A1* | 3/2016 | Crawford | A61B 5/7264 600/301 |

FOREIGN PATENT DOCUMENTS

| | | |
|---|---|---|
| CN | 1460373 A | 12/2003 |
| CN | 103324720 A | 9/2013 |
| JP | 2005032167 A | 2/2005 |

* cited by examiner

*Primary Examiner* — Bryan Lee
(74) *Attorney, Agent, or Firm* — Young Basile Hanlon & MacFarlane, P.C.

(57) ABSTRACT

A method, an apparatus, and a system for pushing network content includes receiving an identity of a user and a current status parameter of the user, acquiring user information associated with the identity including personal information of the user and a browsing history of the user, selecting network content according to the status parameter and the user information, and pushing the network content to a terminal device configured to display the network content.

20 Claims, 5 Drawing Sheets

METHOD, APPARATUS, AND SYSTEM FOR PUSHING NETWORK CONTENT

CROSS-REFERENCE TO RELATED APPLICATION

This application claims priority to Chinese patent application no. CN 201410531591. 5, filed Oct. 10, 2014, which is incorporated herein in its entirety by reference.

TECHNICAL FIELD

The present disclosure relates to the field of Internet technologies, and in particular, to a method, apparatus, and system for pushing network content.

BACKGROUND

With the rapid development of Internet technologies, mobile online and Internet interaction have become part of people's daily life. Many users interact with the Internet constantly. For them, finding and presenting content on the Internet more efficiently has become an important issue.

SUMMARY

In some solutions, network content can be selected for a user according to historical behaviors and habits of the user. For example, for a user who often watches videos about swimming competitions, when the user visits the same website again, the latest videos about swimming competitions can be recommended to the user. Or, when the user visits a shopping website, products related to swimming articles can be recommended to the user. However, selecting network content for a user according to behaviors and habits of the user can fail to detect the current status of the user, and the result of selection might not be accurate.

Implementations of the present disclosure provide a method, apparatus, and system for pushing network content, which can be used to present users with currently needed network content.

A method for pushing network content includes receiving an identity of a user and a current status parameter of the user, acquiring user information associated with the identity, the user information including personal information of the user and a browsing history of the user, selecting network content according to the status parameter and the user information, and pushing the network content to a terminal device, the terminal device configured to display the network content.

In some implementations, since network content is selected for the user based on the current status parameter of the user and the browsing history of the user, various aspects can be taken into consideration for recommending network content to the user, so that network content that is currently needed by users can be presented more accurately.

Optionally, the status parameter includes a current motion status and sleep status of the user.

In the optional solution, since network content is selected for the user based on the current motion status, sleep status of the user and the browsing history of the user, various aspects can be taken into consideration for recommending network content to the user, so that network content that is currently needed by users can be presented more accurately.

Optionally, the status parameter further includes a current heart rate of the user, and the selecting network content according to the status parameter and the user information includes determining whether the current heart rate of the user reaches a preset threshold, determining whether the current motion status of the user is a preset motion status based on a determination that the current heart rate of the user reaches the preset threshold, and selecting network content according to the determined current motion status and the user information.

In the optional solution, since network content is selected for the user based on the current heart rate and motion status of the user and the browsing history of the user, various aspects can be taken into consideration for recommending network content to the user, so that network content that is currently needed by users can be presented more accurately.

Optionally, prior to receiving an identity of a user and a current status parameter of the user, the method further includes associating the identity and the user information, and storing the associated identity and user information.

In the optional solution, user information can be acquired according to a pre-stored association, so that video content can be recommended to the user more accurately.

Optionally, the method further includes recording the current status parameter of the user and current browsing content of the user, associating the current status parameter of the user and the current browsing content of the user, storing the associated browsing content in a browsing history corresponding to the user information, updating the browsing history corresponding to the user information.

In the optional solution, the current status parameter and the current browsing content of the user are associated and stored, so that the current browsing history of the user can be updated in real time, and network content can be recommended to the user more accurately.

In one aspect, a method for pushing network content includes identifying a current status parameter of a user, the status parameter including a current motion status and sleep status of the user and a current heart rate of the user, and sending the status parameter and an identity of the user.

In some implementations, the current status parameter of the user can be detected, so that when selecting network content for the user, a network side selects network content for the user based on the current status parameter of the user and the browsing history of the user. Thus, various aspects can be taken into consideration for recommending network content to the user, so that network content that is currently needed by users can be presented more accurately.

An apparatus for pushing network content includes a receiving module configured to receive an identity of a user and a current status parameter of the user, an acquisition module configured to acquire user information associated with the identity, the user information including personal information of the user and a browsing history of the user. The apparatus further includes a selection module configured to select network content according to the status parameter and the user information, and a push module configured to push the network content to a terminal device, the terminal device configured to display the network content.

Optionally, the selection module includes a first determining unit, configured to determine whether a current heart rate of the user reaches a preset threshold. The selection module further includes a second determining unit, configured to determine whether a current motion status of the user is a preset motion status when the current heart rate of the user reaches the preset threshold. The selection module further includes a selection unit configured to select network content according to a determining result and the user information.

Optionally, the apparatus further includes a first association module configured to associate the identity and the user information, and a first storage module, configured to store the associated identity and user information.

Optionally, the apparatus further includes a recording module, configured to record the current status parameter of the user and current browsing content of the user, a second association module configured to associate the current status parameter of the user and the current browsing content of the user, a second storage module configured to store the associated browsing content in a browsing history corresponding to the user information, and an update module configured to update the browsing history corresponding to the user information.

In another aspect, an apparatus for pushing network content includes an identification module configured to identify a current status parameter of a user. The status parameter includes, for example, a current motion status and sleep status of the user and a current heart rate of the user. The status parameter further includes a sending module configured to send the status parameter and an identity of the user.

In another aspect, a system for pushing network content, including a server, a terminal device, and a smart band. The server is configured to receive an identity of a user and a current status parameter of the user, acquire user information associated with the identity, the user information including personal information of the user and a browsing history of the user. The server is further configured to select network content according to the status parameter and the user information, and push the network content to a terminal device, the terminal device being configured to display the network content.

The terminal device is configured to receive the network content pushed by the server; and display the network content, and the smart band is configured to identify the current status parameter of the user. The status parameter includes, for example, a current motion status, a sleep status, and a current heart rate of the user, or any combination thereof. The terminal device is further configured to send the status parameter and the identity of the user.

Optionally, the terminal device is further configured to receive the identity of the user and the current status parameter of the user, and send the identity and the current status parameter of the user to the server.

Other features and advantages of the present disclosure will be set forth in the description which follows, and in part will be obvious from the description, or may be learned by practice of the present disclosure. The objectives and other advantages of the present disclosure can be realized and attained by the structure particularly pointed out in the written description, claims and the accompanying drawings.

The technical solutions of the present disclosure will be described in further detail hereinafter with reference to the accompanying drawings and implementations.

BRIEF DESCRIPTION OF THE DRAWINGS

The accompanying drawings, which are included to provide a further understanding of the present disclosure and are incorporated in and constitute a part of this specification, serve to explain the present disclosure together with implementations of the present disclosure, but are not intended to limit the present disclosure. In the drawings.

DETAILED DESCRIPTION

Certain implementations of the present disclosure will be described hereinafter with reference to the accompanying drawings. It should be appreciated that the preferred implementations described herein are merely used for describing and explaining the present disclosure, and are not intended to limit the present disclosure.

Figure 1:
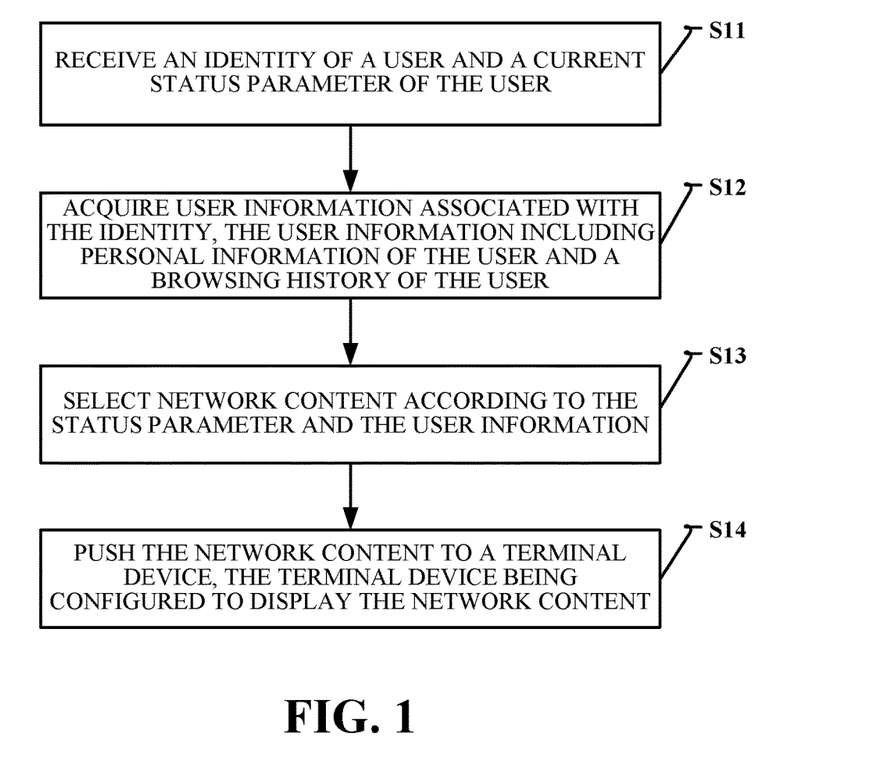
FIG. 1 is a flowchart of a method for pushing network content according to an implementation of the present disclosure.

An implementation of the present disclosure provides a method for pushing network content, which is used to present users with currently needed network content. As shown in FIG. 1, the method includes steps S11-S14 described as follows.

At Step S11, an identity of a user and a current status parameter of the user is received.

At Step S12, user information associated with the identity can be acquired. The user information can include, for example, personal information of the user and a browsing history of the user. The personal information of the user can include, for example, the age, gender, interests and other information of the user.

At Step S13, network content is selected according to the status parameter and the user information.

At Step S14, the network content can be pushed to a terminal device, the terminal device being configured to display the network content.

Since network content is selected for the user on the basis of the current status parameter of the user and the browsing history of the user, various aspects can be taken into consideration for recommending network content to the user, so that network content that is currently needed by users can be presented more accurately.

In one implementation, in step S11, the current status parameter of the user can include, for example, a current motion status, a sleep status of the user, or both. The identity of the user may be directly stored in a smart wearable device such as a smart band (e.g., wristband or ring), or may be stored in the smart wearable device in the form of a data packet. The smart wearable device can include a Bluetooth chip installed therein, and can send the identity of the user or the data packet containing the identity of the user via Bluetooth. The terminal device (e.g., a smart television, a smart phone, or a computer) receives and parses the data packet to obtain the identity of the user and sends the identity of the user to a network side (e.g., a server), or the network side can directly receive and parse the data packet to obtain the identity of the user.

Moreover, when the identity of the user is stored in a smart wearable device in the form of a data packet, the smart wearable device can include, for example, a motion tracker and a sleep tracker installed therein, where the motion tracker is configured to detect the current motion status of the user. For example, the motion tracker can be configured to detect that the user is running, and the sleep tracker can be used to detect the current sleep status of the user (e.g., the user just got up). The smart wearable device detects and sends the current status parameter of the user. The terminal device (e.g., a smart television, a smart phone, or a computer) receives the current status parameter of the user and forwards the current status parameter of the user to the network side, or the network side can directly receive the current status parameter of the user.

For example, when the motion status of the user is "swimming", the network side may recommend network content related to swimming, such as videos about swimming competitions or websites selling swimming articles, to the user according to the browsing history of the user. In another example, when the sleep status of the user is "just got up", the network side may select, according to the browsing history of the user, network content that the user usually browses during this period of time, and then recommend the network content to the user.

In one implementation, the current status parameter of the user further includes, for example, a current heart rate of the user, in addition to the current motion status or the sleep status of the user. In this case, step S13 can be further implemented in steps S131-S133 as follows.

At Step S131, it is determined whether the current heart rate of the user reaches a preset threshold. For example, assuming the normal heart rate of the user is 70 to 90 beats/minute, the preset threshold can be set to a value slightly higher than 70 to 90 beats/minute. For example, the preset threshold can be set to 120 beats/minute.

At step S132, when the current heart rate of the user reaches the preset threshold, it can be determined whether the current motion status of the user is a preset motion status. The preset motion status can be a factor causing the current heart rate of the user to reach the preset threshold. The preset motion status can be associated with, for example, certain activities causing the current heart rate of the user to reach a certain preset threshold. For example, the preset motion status can include, for example, running, swimming, or cycling.

At step S133, network content can be selected according to the determined current motion status from step S132, and the user information. If it is determined that the current motion status of the user is a preset motion status, it can be indicated that the current increase in heart rate of the user caused by exercise, and accordingly network content related to exercise can be selected for the user.

If it is determined that the current motion status of the user is not the preset motion status, it can be indicated that the current increase in heart rate of the user is irrelevant to exercise. Thus, it can be estimated that the current increase in the heart rate of the user is caused by emotional fluctuation, and accordingly, network content that can relieve emotional stress may be selected for the user. For example, when the user visits a shopping website or is near a shopping store, discounts, coupons or similar promotions may be recommended to the user to stimulate user consumption to help the user relieve emotional stress.

In one implementation, prior to performing step S11, one or more of the following steps may be performed, such as associating the identity and the user information, and storing the associated identity and user information.

In one implementation, the method further includes, for example, steps S15-S18 as follows.

At step S15, the current status parameter of the user and current browsing content of the user are recorded.

At step S16, Associate the current status parameter of the user and the current browsing content of the user can be associated.

At step S17, the associated browsing content can be stored in a browsing history corresponding to the user information.

At step S18, the browsing history can be updated corresponding to the user information.

Figure 2:
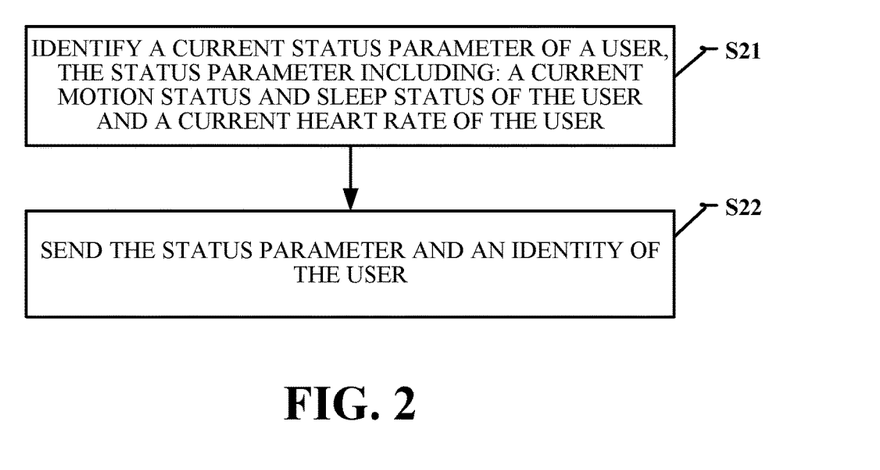
FIG. 2 is a flowchart of a method for pushing network content according to another implementation of the present disclosure.

Further, an implementation of the present disclosure provides a method for pushing network content, as shown in FIG. 2. The method can include, for example, the following steps S21-S22.

At step S21, a current status parameter of a user is identified. For example, the status parameter includes a current motion status of the user, a sleep status of the user, a current heart rate of the user, or any combination of the above.

At step S22, the status parameter and an identity of the user are sent. The status parameter and the identity of the user are sent to, for example, a network side (e.g., server) or a terminal device.

For example, the method may be applied to a smart wearable device such as a smart band described above. The smart wearable device can be used to identify the current status parameter of the user, and send the status parameter and the identity of the user to a terminal device (for example, a smart television, a smart phone, or a computer), or the network side. When the smart wearable device sends the status parameter and the identity of the user to the terminal device, the terminal device forwards the status parameter and the identity of the user to the network side. Then, the network side recommends network content to the user according to the received status parameter and identity of the user. When identifying the current status parameter of the user, the smart wearable device can perform the identification by using a motion tracker, a sleep tracker or a heart rate tracker installed therein, or any combination of the above.

In this implementation, the current status parameter of the user can be detected, so that when selecting network content for the user, the network side selects network content for the user based on the current status parameter of the user and the browsing history of the user. Thus, various aspects can be taken into consideration for recommending network content to the user, so that network content that is currently needed by users can be presented more accurately.

Figure 3:
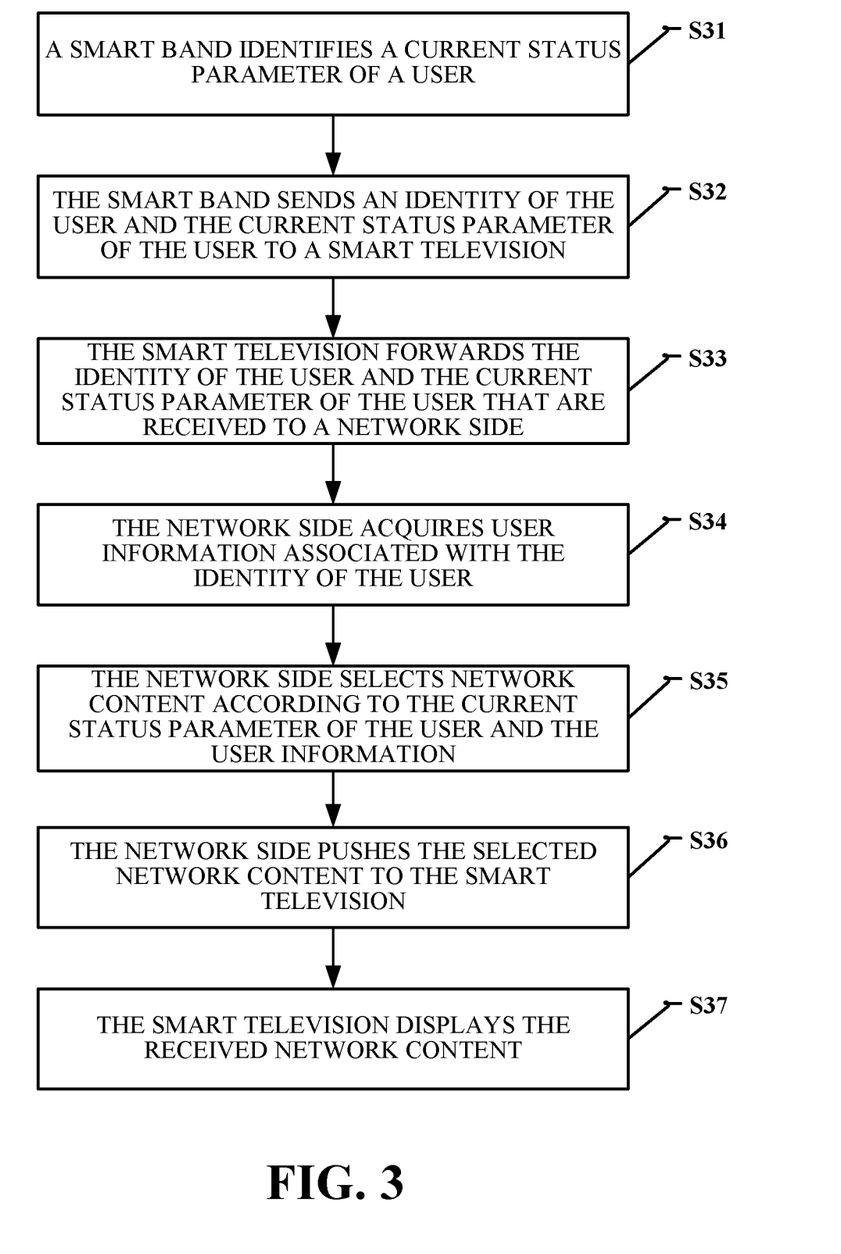
FIG. 3 is a flowchart of a method for pushing network content according to an implementation of the present disclosure.

FIG. 3 is a flowchart of a method for pushing network content according to an implementation of the present disclosure. In this implementation, the identity of the user is stored in a smart band. As shown in FIG. 3, the method includes, for example, the following steps S31-S37.

At step S31, a smart band identifies a current status parameter of a user, for example, a status indicating that the user is swimming.

At step S32, the smart band sends an identity of the user and the current status parameter of the user to a terminal device, such as a smart television.

At step S33, the smart television forwards the identity of the user and the current status parameter of the user that are received to a network side.

At step S34, the network side acquires user information associated with the identity of the user. The user information can include, for example, personal information of the user, a browsing history of the user, or any combination of the above.

At step S35, the network side selects network content according to the current status parameter of the user and the user information.

At Step S36, the network side pushes the selected network content to the terminal device, such as the smart television.

At Step S37, the terminal device, such as the smart television, displays the received network content.

In this implementation, the smart band detects the current status parameter of the user and sends the current status parameter of the user to the network side, so that when selecting network content for the user, the network side selects network content for the user based on the current status parameter of the user and the browsing history of the user. Thus, various aspects can be taken into consideration for recommending network content to the user, so that network content that is currently needed by users can be presented more accurately.

Figure 4:
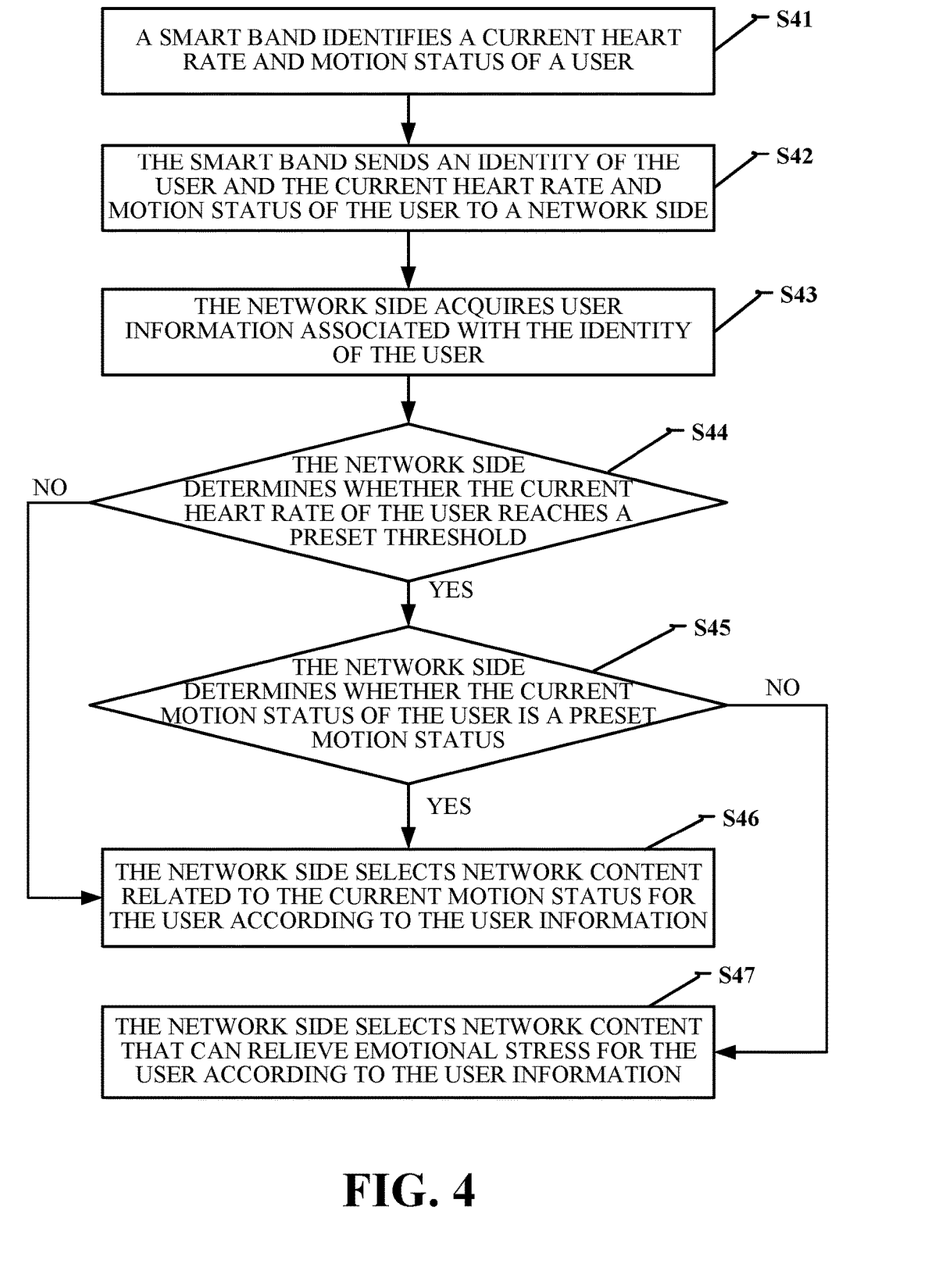
FIG. 4 is a flowchart of a method for pushing network content according to another implementation of the present disclosure.

FIG. 4 is a flowchart of a method for pushing network content according to another implementation of the present disclosure. In this implementation, the identity of the user is stored in a smart band, and the smart band identifies the current heart rate and motion status of the user. As shown in FIG. 4, the method includes, for example, the following steps S41-S47.

At step S41, a smart band identifies a current heart rate and motion status of a user.

At step S42, the smart band sends an identity of the user and the current heart rate and motion status of the user to a network side.

At step S43, the network side acquires user information associated with the identity of the user.

At step S44, the network side determines whether the current heart rate of the user reaches a preset threshold. For example, assuming that the preset threshold is set to 120 beats/minute, if the current heart rate of the user reaches the preset threshold of 120 beats/minute, step S45 is performed. If the current heart rate of the user does not reach the preset threshold of 120 beats/minute, step S46 is performed.

At step S45, the network side determines whether the current motion status of the user is a preset motion status. For example, assuming that the preset motion status includes, for example, swimming and running, if the current motion status of the user is a preset motion status, step S46 is performed. If the current motion status of the user is not the preset motion status, step S47 is performed.

At step S46, the network side selects network content related to the current motion status for the user according to the user information.

At step S47, the network side selects network content for the user according to the user information. The selection can be configured to help relieve emotional stress of the user.

In this implementation, the smart band detects the current heart rate and motion status of the user, so that the network side can select network content for the user based on the current heart rate and motion status of the user and the browsing history of the user. Thus, various aspects can be taken into consideration for recommending network content to the user, so that network content that is currently needed by users can be presented more accurately.

Figure 5:
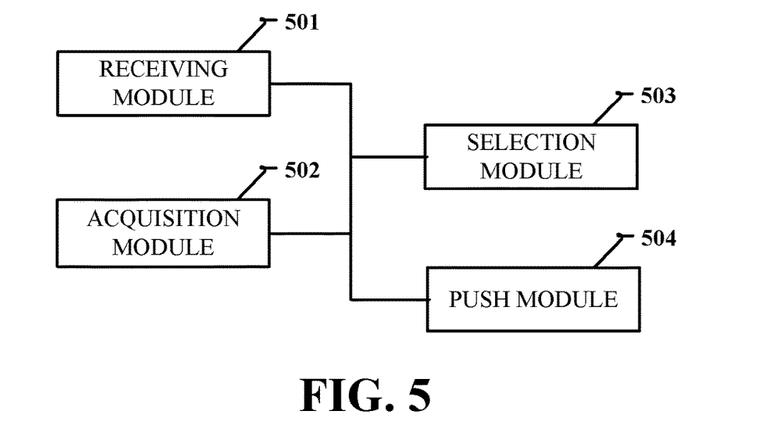
FIG. 5 is a block diagram of an apparatus for pushing network content according to an implementation of the present disclosure.

Corresponding to the method provided in the implementations of the present disclosure, an implementation of the present disclosure further provides an apparatus for pushing network content, as shown in FIG. 5. The apparatus includes, for examples, the following modules 501 to 504, which can be implemented by software, or hardware, or an implementation combining software and hardware aspects.

The apparatus can include a receiving module 501, configured to receive an identity of a user and a current status parameter of the user.

The apparatus can further include an acquisition module 502, configured to acquire user information associated with the identity, the user information including personal information of the user and a browsing history of the user.

The apparatus can further include a selection module 503, configured to select network content according to the status parameter and the user information.

The apparatus can further include a push module 504, configured to push the network content to a terminal device, the terminal device configured to display the network content.

In one implementation, the selection module 503 includes, for example, a first determining unit, configured to determine whether a current heart rate of the user reaches a preset threshold.

The selection module 503 further includes a second determining unit, configured to determine whether a current motion status of the user is a preset motion status when the current heart rate of the user reaches the preset threshold. The selection module 503 further includes a selection unit, configured to select network content according to a determining result and the user information.

Figure 6:
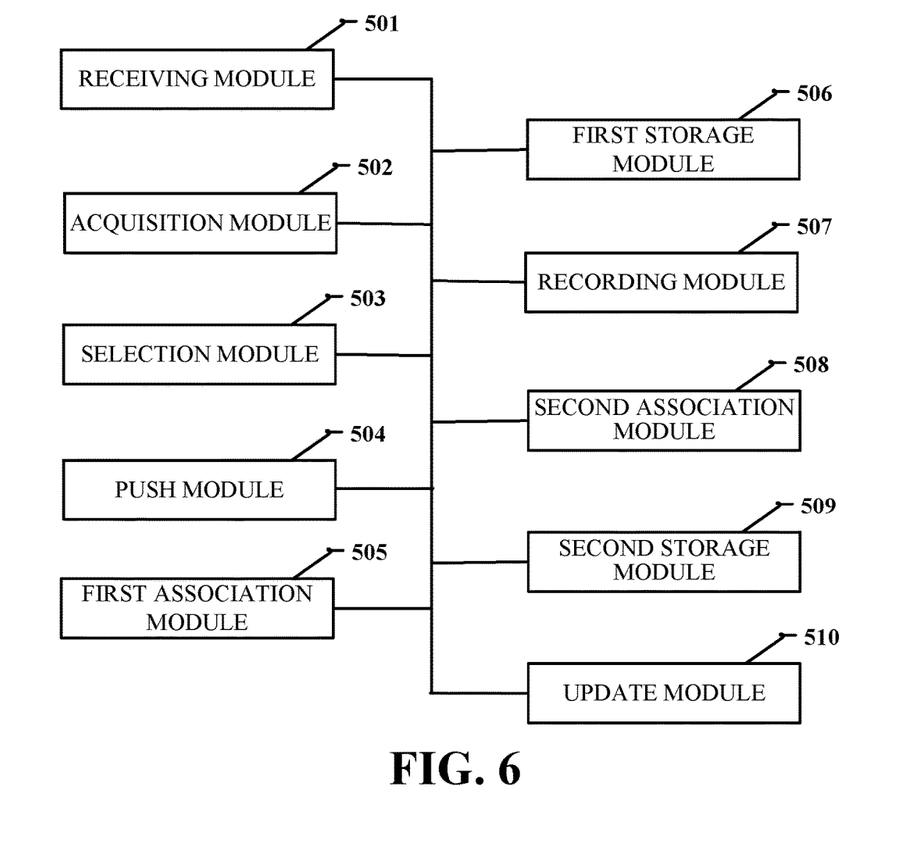
FIG. 6 is a block diagram of an apparatus for pushing network content according to another implementation of the present disclosure.

In one implementation, as shown in FIG. 6, the apparatus further includes, for example, modules 505-510 described below. The apparatus includes a first association module 505, configured to associate the identity and the user information. The apparatus further includes a first storage module 506, configured to store the associated identity and user information. The apparatus further includes a recording module 507, configured to record the current status parameter of the user and current browsing content of the user. The apparatus further includes a second association module 508, configured to associate the current status parameter of the user and the current browsing content of the user. The apparatus further includes a second storage module 509, configured to store the associated browsing content in a browsing history corresponding to the user information. The apparatus further includes an update module 510, configured to update the browsing history corresponding to the user information.

In this implementation of the present disclosure, since network content is selected for the user on the basis of the current status parameter of the user and the browsing history of the user, various aspects can be taken into consideration for recommending network content to the user, so that network content that is currently needed by users can be presented more accurately.

Figure 7:
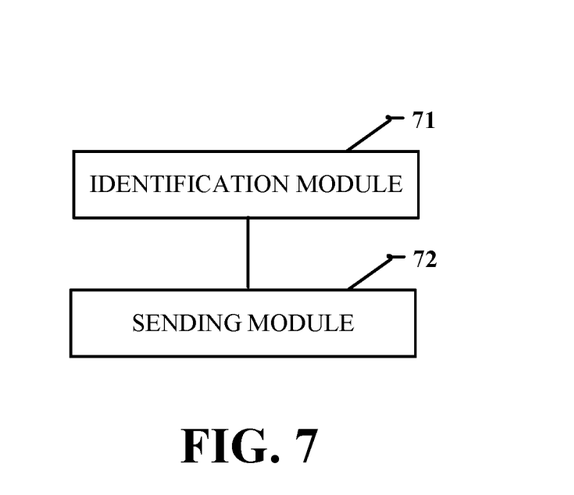
FIG. 7 is a block diagram of an apparatus for pushing network content according to another implementation of the present disclosure.

FIG. 7 is a block diagram of an apparatus for pushing network content according to another implementation of the present disclosure. The apparatus can include, for example, an identification module 71, configured to identify a current status parameter of a user. The status parameter can include, for example, one of a current motion status, a sleep status, a current heart rate of the user, or any combination of the above. The apparatus further includes a sending module 72, configured to send the status parameter and an identity of the user.

In this implementation, the current status parameter of the user can be detected, so that when selecting network content for the user, a network side selects network content for the user based on the current status parameter of the user and the browsing history of the user. Thus, various aspects can be taken into consideration for recommending network content to the user, so that network content that is currently needed by users can be presented more accurately.

Figure 8:
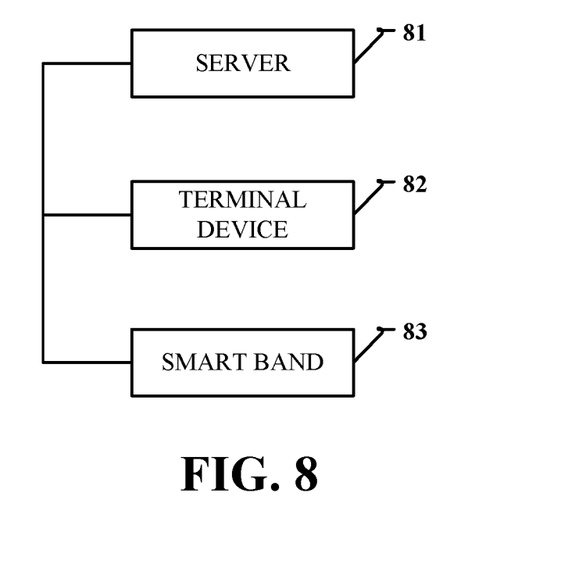
FIG. 8 is a block diagram of a system for pushing network content according to an implementation of the present disclosure.

An implementation of the present disclosure further provides a system for pushing network content, as shown in FIG. 8. The system can include, for example, a server 81, a terminal device 82, and a smart band 83.

The server 81 can be configured to receive an identity of a user and a current status parameter of the user, to acquire user information associated with the identity, the user information including personal information of the user and a browsing history of the user, to select network content according to the status parameter and the user information, and to push the network content to a terminal device, the terminal device being configured to display the network content.

The terminal device 82 can be configured to receive the network content pushed by the server, and display the network content.

The smart band 83 can be configured to identify the current status parameter of the user, the status parameter including a current motion status and sleep status of the user and a current heart rate of the user, and send the status parameter and the identity of the user.

The smart band can include, for example, a motion tracker, a sleep tracker, a heart rate tracker installed therein, or any combination of the above.

In one implementation, in the system, the terminal device 83 can be further configured to receive the identity of the user and the current status parameter of the user and send the identity and the current status parameter of the user to the server.

It should be understood by a person skilled in the art that the implementations of the present disclosure may be provided as a method, system, or computer program product. Accordingly, the present disclosure may take the form of an entirely hardware implementation, an entirely software implementation, or an implementation combining software and hardware aspects. Furthermore, the present disclosure may take the form of a computer program product that is implemented on one or more computer-usable storage media (including but not limited to disk storage and optical storage) having program code usable by computers stored therein.

The present disclosure is described with reference to flowcharts and/or block diagrams of methods, apparatuses (systems) and computer program products according to the implementations of the present disclosure. It should be understood that each procedure and/or block of the flowcharts and/or block diagrams, and combinations of procedures and/or blocks in the flowcharts and/or block diagrams, can be implemented by computer program instructions. These computer program instructions may be provided to a processor of a general purpose computer, special purpose computer, embedded processing device or other programmable data processing apparatuses to produce a machine, such that the instructions, which are executed via the processor of the computer or other programmable data processing apparatuses, create means for implementing the functions specified in one or more procedures of the flowcharts and/or one or more blocks of the block diagrams.

These computer program instructions may also be stored in a computer-readable memory that can direct a computer or other programmable data processing apparatuses to function in a particular manner, such that the instructions stored in the computer-readable memory produce an article of manufacture, including instruction means that implement the functions specified in one or more procedures of the flowcharts and/or one or more blocks of the block diagrams.

These computer program instructions may also be loaded onto a computer or other programmable data processing apparatuses to cause a series of operational steps to be performed on the computer or programmable apparatuses to produce a computer implemented process such that the instructions which are executed on the computer or programmable apparatuses provide steps for implementing the functions in one or more procedures of the flowcharts and/or one or more blocks of the block diagrams.

It is obvious to a person skilled in the art that various variations and modifications can be made to the present disclosure without departing from the spirit and scope of the present disclosure. Therefore, it is intended that these variations and modifications made to the present disclosure be encompassed by the present disclosure, as long as they fall within the scope of the claims of the present disclosure and their equivalents.

What is claimed is:

1. A method for pushing network content, comprising:
   receiving an identity of a user and a current status parameter of the user, wherein the current status parameter comprises a current motion status and a current heart rate detected by a wearable device associated with the user;
   acquiring user information associated with the identity, the user information comprising personal information of the user and a browsing history of the user;
   determining whether the current heart rate reaches a preset threshold;
   in response to determining that the current heart rate reaches the preset threshold, determining whether the current motion status is associated with a first activity predetermined to cause the current heart rate to reach the preset threshold;
   in response to determining that the current heart rate does not reach the preset threshold, selecting, based on the user information, network content associated with a second activity predetermined not to cause the current heart rate of the user to reach the preset threshold;
   based on a determination that the current heart rate reaches the preset threshold and the current motion status is associated with the first activity, selecting, based on the user information, network content associated with the first activity;
   based on a determination that the current heart rate reaches the preset threshold and the current motion status is not associated with the first activity, selecting, based on the user information, network content associated with an emotion of the user predetermined to cause the current heart rate to reach the preset threshold, wherein the emotion of the user is indicative of at least one of an emotional fluctuation and an emotional stress; and
   pushing the network content to a terminal device configured to display the network content.

2. The method of claim 1, wherein the first activity comprises at least one of running, cycling, swimming, and exercising.

3. The method of claim 1, further comprising:
   associating the identity and the user information; and
   storing the associated identity and user information prior to receiving the identity of the user and the current status parameter of the user.

4. The method of claim 1, further comprising:
recording the current status parameter of the user and current browsing content of the user;
associating the current status parameter of the user and the current browsing content of the user;
storing the associated browsing content in a browsing history corresponding to the user information; and
updating the browsing history corresponding to the user information.

5. The method of claim 4, wherein the browsing history corresponding to the user information is updated in real time.

6. The method of claim 1, wherein the first activity is one of multiple activities associated with the current motion status, and the preset threshold is one of multiple preset thresholds, wherein each of the multiple activities is predetermined to cause the current heart rate to reach one of the multiple preset thresholds.

7. The method of claim 1, wherein the current status parameter further comprises a sleep status.

8. The method of claim 7, wherein the second activity comprises at least one of: sleeping, waking up from sleeping, browsing a shopping website, and being near a shopping store.

9. The method of claim 1, wherein the preset threshold comprises at least one of 70 beats per minute, 90 beats per minute, and 120 beats per minute.

10. The method of claim 1, wherein the network content associated with the first activity comprises at least one of: a video associated with the first activity, a website associated with the first activity, a product associated with the first activity, and contents associated with a browsing history associated with a time period when the user performs the first activity.

11. The method of claim 1, wherein the network content associated with the emotion of the user comprises at least one of: a discount, a coupon, a promotion, contents to stimulate user consumption, and contents to relieve emotional stress of the user.

12. An apparatus for pushing network content, comprising:
a processor; and
a memory coupled to the processor, the memory configured to store instructions which when executed by the processor become operational with the processor to:
receive, from a wearable device associated with a user, an identity of the user and a current status parameter of the user, wherein the current status parameter comprises a current motion status and a current heart rate detected by the wearable device;
acquire user information associated with the identity, the user information comprising personal information of the user and a browsing history of the user;
determine whether the current heart rate reaches a preset threshold;
in response to determining that the current heart rate reaches the preset threshold, determine whether the current motion status is associated with a first activity predetermined to cause the current heart rate to reach the preset threshold;
in response to determining that the current heart rate does not reach the preset threshold, select, based on the user information, network content associated with a second activity predetermined not to cause the current heart rate of the user to reach the preset threshold;
based on a determination that the current heart rate reaches the preset threshold and the current motion status is associated with the first activity, select, based on the user information, network content associated with the first activity;
based on a determination that the current heart rate reaches the preset threshold and the current motion status is not associated with the first activity, select, based on the user information, network content associated with an emotion of the user predetermined to cause the current heart rate to reach the preset threshold, wherein the emotion of the user is indicative of at least one of an emotional fluctuation and an emotional stress; and
push the network content to a terminal device configured to display the network content.

13. The apparatus of claim 12, wherein the memory further comprises instructions which when executed by the processor become operational with the processor to:
record the current status parameter of the user and current browsing content of the user;
associate the current status parameter of the user and the current browsing content of the user;
store the associated browsing content in a browsing history corresponding to the user information; and
update the browsing history corresponding to the user information.

14. The apparatus of claim 13, wherein the browsing history corresponding to the user information is updated in real time.

15. The apparatus of claim 12, wherein the terminal device comprises at least one of: a television, a phone, and a computer.

16. The apparatus of claim 12, wherein
the first activity comprises at least one of running, cycling, swimming, and exercising; and
the second activity comprises at least one of: sleeping, waking up from sleeping, browsing a shopping website, and being near a shopping store.

17. A system for pushing network content, comprising:
a wearable device associated with a user;
a terminal device associated with the wearable device; and
a server comprising a processor and a memory coupled to the processor, the memory configured to store instructions which when executed by the processor become operational with the processor to:
receive, from one of the wearable device and the terminal device, an identity of the user and a current status parameter of the user, wherein the current status parameter comprises a current motion status and a current heart rate detected by the wearable device;
acquire user information associated with the identity, the user information comprising personal information of the user and a browsing history of the user;
determine whether the current heart rate reaches a preset threshold;
in response to determining that the current heart rate reaches the preset threshold, determine whether the current motion status is associated with a first activity predetermined to cause the current heart rate to reach the preset threshold;
in response to determining that the current heart rate does not reach the preset threshold, select, based on the user information, network content associated with a second activity predetermined not to cause the current heart rate of the user to reach the preset threshold;

based on a determination that the current heart rate reaches the preset threshold and the current motion status is associated with the first activity, select, based on the user information, network content associated with the first activity;

based on a determination that the current heart rate reaches the preset threshold and the current motion status is not associated with the first activity, select, based on the user information, network content associated with an emotion of the user predetermined to cause the current heart rate to reach the preset threshold, wherein the emotion of the user is indicative of at least one of an emotional fluctuation and an emotional stress; and push the network content to the terminal device, wherein the terminal device is configured to display the network content.

18. The system of claim 17, wherein the first activity comprises at least one of running, cycling, swimming, and exercising.

19. The system of claim 17, wherein the terminal device is further configured to:

receive the identity of the user and the current status parameter of the user from the wearable device; and send the identity and the current status parameter of the user to the server.

20. The system of claim 17, wherein the wearable device comprises a motion tracker installed in the wearable device, a sleep tracker installed in the wearable device, and a heart rate tracker installed in the wearable device.

* * * * *